United States Patent [19]

Watanabe et al.

[11] 4,435,220

[45] Mar. 6, 1984

[54] TRANSPARENT COLORED PIGMENTS

[75] Inventors: Takaji Watanabe, Ohmiya; Tamio Noguchi, Atsugi, both of Japan

[73] Assignee: Merck Patent Gesellschaft mit Beschrankter Haftung, Darmstadt, Fed. Rep. of Germany

[21] Appl. No.: 436,861

[22] Filed: Oct. 26, 1982

[30] Foreign Application Priority Data

Oct. 26, 1981 [JP] Japan ................................. 56-170148

[51] Int. Cl.³ .......................... C04B 31/00; C09C 1/00
[52] U.S. Cl. ..................................... 106/291; 106/306; 106/308 B
[58] Field of Search ...................... 106/308 B, 306, 291

[56] References Cited

U.S. PATENT DOCUMENTS

| | | | |
|---|---|---|---|
| 3,087,828 | 4/1963 | Linton | 106/291 |
| 3,087,829 | 4/1963 | Linton | 106/291 |
| 3,331,699 | 7/1967 | Marshall et al. | 106/291 |
| 3,342,617 | 9/1967 | Jackson | 106/291 |
| 3,440,075 | 4/1969 | Marshall | 106/291 |
| 3,545,994 | 12/1970 | Lott et al. | 106/306 |
| 3,582,382 | 6/1971 | Watanabe et al. | 106/291 |
| 3,650,790 | 3/1972 | Klenke et al. | 106/291 |
| 3,711,308 | 1/1973 | Brand et al. | 106/291 |
| 3,832,208 | 8/1974 | Jackson | 106/308 Q |
| 3,926,659 | 12/1975 | Bernhard et al. | 106/291 |
| 4,134,776 | 1/1979 | Rieger et al. | 106/291 |

*Primary Examiner*—Helen M. McCarthy
*Attorney, Agent, or Firm*—Millen & White

[57] ABSTRACT

Transparent, colored pigments based on platelet-shaped, transparent substrates, such as mica, talc or glass, are coated with colored metal oxides or metal hydroxides, wherein the metal oxide or hydroxide layer contains 0.1–5% by weight of an alkaline earth metal compound. These new, transparent, colored pigments are prepared by a process in which a platelet-shaped, transparent substrate, such as mica, talc or glass, is coated, in the presence of a base, with a colored metal oxide or hydroxide, and 0.1 to 5% by weight of an alkaline earth metal oxide or hydroxide is incorporated in the layer. The pigments have improved dispersibility, gloss, color power and stability to heat and weathering and also filling and adhesion properties. The pigments can be used for all the customary purposes, especially in cosmetics.

12 Claims, No Drawings

TRANSPARENT COLORED PIGMENTS

BACKGROUND OF THE INVENTION

The present invention relates to transparent, colored pigments based on platelet-shaped transparent substrates, such as mica, talc or glass, which are coated with colored metal oxides or metal hydroxides.

Many types of colored pigments are already used in the production of lacquers, printing inks, plastics, cosmetics and other products. However, almost all of these pigments are opaque. There are indeed some organic pigments which are relatively transparent and also possess a good coloring power. However, these pigments have disadvantages because of their low stability to heat and weathering and their high price. In addition, many organic pigments cannot be used without reservation in cosmetics or in the packaging of foodstuffs, and their transparency is unsatisfactory.

On the other hand, transparent pigments exist which comprise substrate material such as alumina white, precipitated barium sulfate or the like on which an organic pigment has adsorptively been deposited. These pigments, however, can be used only to a limited extent, especially in cosmetics, since they are not sufficiently dispersible and have a poor gloss and inadequate filling and adhesion properties.

SUMMARY OF THE INVENTION

Accordingly, it is an object of this invention to provide transparent colored pigments with improved dispersibility, better gloss, a clearer color and improved stability to heat and weathering.

It is another object, in particular, to provide such pigments whose filling and adhesion properties are also improved for use in cosmetics.

Upon further study of the specification and appended claims, further objects and advantages of this invention will become apparent to those skilled in the art.

These objects have been attained by providing such pigments comprising platelet-shaped, transparent substrates which are coated with a layer of a metal oxide or metal hydroxide, wherein the improvement is effected by additionally including an alkaline earth metal in the coating.

In one aspect, this invention thus relates to transparent, colored pigments based on platelet-shaped, transparent substrates, such as mica, talc or glass, which are coated with colored metal oxides or metal hydroxides, wherein the metal oxide or hydroxide layer contains 0.1-5% by weight of an alkaline earth metal compound.

In another aspect, this invention also relates to a process for the preparation of transparent, colored pigments comprising coating a platelet-shaped, transparent substrate, in aqueous suspension in the presence of a base, with a colored metal oxide or hydroxide precipitate; then separating the substrate off, washing it, if necessary, drying it and, if necessary, calcining it; wherein the metal oxide or hydroxide precipitation is carried out in the presence of an alkaline earth metal compound.

DETAILED DISCUSSION

Suitable platelet-shaped, transparent substrates include mica, such as, for example, muscovite, sericite or phlogopite, and talc platelets and glass platelets. These substrates are as a rule used in particle sizes of about 1-100 $\mu$m, preferably in a size of about 5-50 $\mu$m.

Examples of suitable colored metal oxides or hydroxides include $FeO(OH)$, $Fe(OH)_2$, $Fe(OH)_3$, $Co(OH)_2$, $Cr(OH)_3$, $Fe_2O_3$, $Fe_3O_4$, $CoO$ or $Cr_2O_3$. If desired, colorless metal oxides, such as, for example, $Al_2O_3$, $ZnO$ or $TiO_2$, can also be precipitated at the same time. Unless indicated otherwise herein, all aspects of the substrates coated with the colored metal oxides and the optional colorless metal oxides are fully conventional and are discussed, e.g., in U.S. Pat. Nos. 3,087,828, 3,087,829 and 3,926,659, whose disclosure is incorporated by reference herein.

Calcium oxide and hydroxide and/or magnesium oxide and hydroxide and/or barium oxide and hydroxide are preferably used as the alkaline earth metal compound(s), the other alkaline earth metals such as strontium also being suitable.

All the metal oxides and hydroxides mentioned can be present in the layer either by themselves or in mixtures, and it is also possible for mixed oxides of these metals to be formed. The layer contains about 0.1-5% by weight of the alkaline earth metal compound(s). Inferior results are achieved with less than 0.1% by weight. The properties cannot be improved further by a content of more than 5% by weight.

To prepare the pigments according to this invention, the platelet-shaped, transparent substrate is suspended in an aqueous solution containing both at leas one metal salt and one alkaline earth metal salt. Suspension of the platelets is fully conventional, e.g. simply by shaking or preferably by stirring.

Examples of metal salts which are suitable for the formation of the colored oxides or hydroxides include $FeSO_4$, $FeCl_2$, $Fe(NH_4)_2(SO_4)_2$, $Fe(NO_3)_2$, $Fe_2(SO_4)_3$, $FeCl_3$, $FeNH_4(SO_4)_2$, $Fe(NO_3)_3$, $CoCl_2$, $CoSO_4$, $Co(NO_3)_2$, $CrCl_3$, $Cr_2(SO_4)_3$, $CrNH_4(SO_4)_2$, etc. Examples which may be mentioned of metal salts which are suitable for the optional additional desposition of colorless metal oxides include: $Al_2(SO_4)_3$, $AlNH_4(SO_4)_2$, $AlCl_3$, $Al(NO_3)_3$, $AlNa(SO_4)_2$, $AlK(SO_4)_2$, $ZnCl_2$, $ZnSO_4$, $TiOSO_4$, $TiCl_4$, etc. Examples of suitable alkaline earth metal salts include: $MgSO_4$, $Mg(NO_3)_2$, $MgCl_2$, $MgBr_2$, $MgI_2$, $Mg(OH)_2$, $CaCl_2$, $CaBr_2$, $Ca(OH)_2$ and $CaI_2$. $MgSO_4$, $MgCl_2$ and $CaCl_2$ are particularly preferably used.

All these metal and alkaline earth metal salts can be used in combination with one another, and the proportions of various metal salts and the weight ratio of coating to substrate can be freely chosen according to the desired color, especially for the coating with the colored oxides or hydroxides. Of course, the amount of alkaline earth metal component in solution must be sufficient to provide the desired amount of precipitated oxide or hydroxide.

As a rule, an approximately 5-25% by weight suspension of the platelet-shaped substrate in the solution of the metal salts, which contains about $9 \times 10^{-7}$ to $19 \times 10^{-6}$ moles of metal salts per m$^2$ of substrate surface to be coated, is prepared. The salts are then hydrolyzed by addition of a base, and the metals, together with the alkaline earth metals, are deposited on the substrate in the form of the hydroxides or hydrated oxides.

Examples of suitable bases include aqueous ammonia, ammonium bicarbonate, sodium bicarbonate, potassium bicarbonate, sodium hydroxide solution and potassium hydroxide solution. In addition, however, substances which produce ammonia by hydrolysis in the aqueous suspension, such as urea, acetamide or formamide, can also be used as bases. Urea is particularly preferred, since in this case a particularly fine particle size of the hydrated metal oxides precipitated on the substrate can be achieved, and a particularly good transparency of the product thereby results. Moreover, a particularly homogeneous deposition of the hydrated metal oxides on the substrate is achieved by urea.

The base is added as an approximately 2–10% by weight solution in the course of about 0.5–2 hours, until the suspension is neutral. Thereafter, the mixture should be stirred for about another 30 minutes. If urea is used as the base, about 3–30 equivalents of urea, relative to the metal oxides, is added, and the suspension is boiled for about 0.5–5 hours.

Magnesium hydroxide, calcium hydroxide, iron-II hydroxide, iron-III hydroxide, cobalt hydroxide, chromium hydroxide, aluminum hydroxide, zinc hydroxide, titanium hydroxide, hydrated titanium oxide or hydrated iron oxide, for example, can all be deposited in this manner. When the deposition has ended, the products are separated off, and as a rule washed, and dried at about 100°–120° C. If desired, they can also be calcined, for example at about 400°–900° C. for about 0.5–5 hours, whereby the hydroxides or hydrated oxides are converted into the oxides. Calcining may be desired, for example, to change the color of the pigment or to produce temperature stable pigments.

Since the metal oxides mentioned, with the exception of those of aluminum, zinc and titanium, provide a number of variously colored metal oxides, it is possible to produce both many different colors, such as, for example, red, yellow, blue, green and black, as well as any neutral colorings in between, and also very many color shades by selecting the type of metal oxides or by selecting the mixing proportions of various metal oxides. All of this can be done routinely, perhaps with a few preliminary experiments.

For example, to prepare a yellow, transparent pigment, an approximately 5–25% by weight aqueous suspension of the platelet-shaped substrate, containing about 10–150, preferably about 30–90, parts of an iron salt, 1–50, preferably 2–30, parts of an alkaline earth metal salt and 10–400, preferably 30–270 parts of urea in solution, in each case relative to 100 parts of the substrate, is prepared. This suspension is boiled for about 0.5–5 hours, after which a yellow pigment can be isolated by separating off, washing and drying at about 105°–110° C.

A red, transparent pigment can be prepared therefrom by heating to 300°–1,200° C., preferably 400°–900° C.

To prepare a black, transparent pigment, an approximately 5–25% by weight aqueous suspension of the platelet-shaped substrate, which contains about 50–300, preferably 150–250, parts of an iron salt, 3–90, preferably 15–60, parts of an alkaline earth metal salt, 25–1,500, preferably 75—1,000 parts of urea and 2.5–90, preferably 8–75, parts of potassium nitrate in solution, in each case relative to 100 parts of the substrate, is prepared. After the suspension has been boiled for 0.5–5 hours and the product has been separated off, washed and dried at 100°–110° C., a black, transparent pigment is obtained.

To prepare a green, transparent pigment, an approximately 5–25% by weight aqueous suspension of the platelet-shaped substrate, which contains 20–200, preferably 40–150, parts of a cobalt salt, 20–200, preferably 40–150, parts of an aluminum salt, 7–60, preferably 10–30, parts of an alkaline earth metal salt and 100–800, preferably 200–450, parts of urea in solution, in each case relative to 100 parts of the substrate, is prepared. After the suspension has been boiled for 0.5–5 hours and the product has been separated off, washed, dried at about 120° C. and calcined at about 500°–700° C., a green, transparent pigment is obtained.

A blue, transparent pigment is obtained therefrom by calcining at 800°–1,200° C.

The pigments thus obtained have excellent dispersibility, gloss, clarity of color and stability to heat, and can be used for any of the numerous conventional applications, in particular in cosmetics wherein they are contained usually in amount of 0.1–80 wt.%.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

Example 1

A solution of 55 g of iron-III ammonium sulfate, 10 g of magnesium sulfate and 80 g of urea in 900 ml of water, in which 90 g of mica of a particle size 1–10 $\mu$m is suspended, is heated to 95°–98° C. for one hour. The product is then separated off, washed with water and dried at 105°–110° C. A pigment is obtained which has the yellow color of iron oxide hydroxide and a good transparency and dispersibility.

EXAMPLE 2

A solution of 7.5 g of iron-III ammonium sulfate, 1.5 g of magnesium sulfate and 20 g of urea in 100 ml of water, in which 10 g of talc is suspended, is heated to 95°–98° C. for 1 hour. The product formed is separated off, washed with water and dried at 105°–110° C. The pigment formed, which is an iron oxide hydroxide deposited on talc, has a yellow color and a good dispersibility.

EXAMPLE 3

A solution of 80 g of iron-III ammonium sulfate, 18 g of magnesium sulfate and 162 g of urea in 900 ml of water, which contains 90 g of suspended mica of a particle size 1–10 $\mu$m is heated to 95°–98° C. for one hour. The product is separated off, washed with water and dried at 105°–110° C. The pigment formed is yellow ochre and has a good transparency and dispersibility.

EXAMPLE 4

A solution of 64 g of iron-III chloride, 13 g of magnesium sulfate and 128 g of urea in 900 ml of water which contains 90 g of dispersed mica of particle size 1–10 $\mu$m is heated to 95°–98° C. for 2 hours. The product is then filtered off, washed and dried at 105°–110° C. for 8 hours. A yellow ochre-colored pigment with good transparency and dispersibility is obtained.

EXAMPLE 5

The pigment prepared according to Example 4 is calcined at 700° C. for 1 hour. A red, transparent pigment is obtained.

EXAMPLE 6

A solution of 128 g of iron-III chloride, 26 g of magnesium sulfate and 256 g of urea in 900 ml of water which contains 90 g of dispersed mica of a particle size 1–10 μm is heated to 95°–98° C. for 2 hours. After filtration, washing with water and drying at 105°–110° C. for 8 hours, a yellow ochre-colored pigment with good transparency and dispersibility is obtained.

EXAMPLE 7

The pigment prepared according to Example 6 is calcined at 700° C. for one hour. A violet-red, transparent pigment is obtained.

EXAMPLE 8

A solution of 178 g of iron-II sulfate, 40 g of magnesium sulfate, 32 g of potassium nitrate and 300 g of urea in 900 ml of water which contains 80 g of dispersed mica of particle size 1 to 10 μm is heated to 95°–98° C. for 4 hours. After filtration, washing with water and drying at 105°–110° C. for 10 hours, a black pigment with good transparency and dispersibility is obtained.

EXAMPLE 9

A solution of 3.0 g of aluminum chloride, 3.0 g of cobalt chloride, 1.0 g of magnesium sulfate and 20 g of urea in 60 ml of water which contains 5.0 g of dispersed mica of particle size 1–10 μm is heated to 95°–98° C. for 2 hours. The product is filtered off, washed with water and dried at 105°–110° C. for 2 hours. After the whitish product which has been formed has been calcined at 600° C. for one hour, a transparent green pigment is obtained.

EXAMPLE 10

The whitish pigment prepared according to Example 9 is calcined at 800° C. for on hour. A blue, transparent pigment is obtained.

EXAMPLE 11

A solution of 20 g of iron-III chloride in 300 ml of water which contains 30 g of dispersed mica of particle size 1–10 μm is heated to 78°–82° C. for one hour, and 85 ml of a 10% sodium hydroxide solution is then added in the course of 0.5 hour. 100 ml of a 6% calcium chloride solution is added to the solution, which has a pH value of 2.3, in the course of 5 minutes, and 10% sodium hydroxide solution is then added in an amount such that a neutral pH value is achieved. The product is separated off, washed with water and dried at 105°–110° C. for 2 hours. After calcining at 700° C. for one hour, a red, transparent pigment is obtained.

EXAMPLE 12

A solution of 3.0 g of chromium-III sulfate, 1.0 g of magnesium sulfate and 10.0 g of urea in 150 ml of water which contains 10 g of dispersed mica of particle size 1–10 μm is heated to 95°–98° C. for 0.5 hour. The product is filtered off, washed with water and dried at 98°–105° C. for 5 hours. After the pale green product has been calcined at 800° C. for one hour, a blue-green, transparent pigment is obtained.

EXAMPLE 13

A solution of 2.0 g of zinc chloride, 2.0 g of iron-III chloride, 0.5 g of magnesium sulfate and 20 g of urea in 100 ml of water which contains 5.0 g of dispersed mica of particle size 1 to 10 μm is heated to 95°–98° C. for one hour. The product is filtered off, washed with water and dried at 98°–105° C. for 10 hours. After the product has been calcined at 800° C. for one hour, a yellow ochre-colored, transparent pigment is obtained.

EXAMPLE 14

A suspension of 5 g of mica of particle size 1–10 μm in 50 ml of water is heated to 95°–98° C. for 5 minutes, a solution of 20 g of titanyl sulfate, 4 g of magnesium sulfate and 40 g of urea in 100 ml of water is then added in the course of 80 minutes, and stirring is continued for one hour. After the whitish product thereby obtained has been calcined at 800° C. for 1 hour, a transparent pigment with a blue-green interference color is obtained.

Comparison Example 1

A solution of 128 g of iron-III chloride and 256 g of urea in 900 ml of water which contains 90 g of dispersed mica of particle size 1–10 μm is heated to 95°–98° C. for 2 hours. After filtration, washing with water, drying at 105°–110° C. for 8 hours and calcining at 700° C. for one hour, a violet-red pigment is obtained. The dispersibility of this product is compared with that of the product according to Example 7 by the following method: 45 g of a standard lacquer base (VS medium ink) is introduced into a 300 ml glass beaker and 5.0 g of the particular pigment is stirred in at a speed of 500 rpm. In each case after 5, 10, 30 and 60 minutes, samples are taken and are brushed onto covering paper which has a white field and a black field. The dispersibility of the particular pigments can be evaluated with the aid of the samples thus obtained. While the pigment according to Example 7 is already dispersed very well after 5 minutes, the comparison pigment is still not adequately dispersed even after 60 minutes.

Comparison Example 2

A solution of 178 g of iron-II sulfate, 32 g of potassium nitrate and 300 g of urea in 900 ml of water which contains 80 g of dispersed mica of a particle size of 1–10 μm is heated to 95°–98° C. for 4 hours, and the product is then filtered off, washed with water and dried at 98°–105° C. for 10 hours. The stability to heat and stability to oxidation of this sample is determined by measuring the TGA and DTA values with the aid of an apparatus manufactured by Shinku-Rikoh Kabushiki Kaisha, Model AGNE, TGD-1500. The result shows that the TGA and DTA curves change at 155° C., at which point the color shade of the pigment changes from black to red-brown with conversion of $Fe_3O_4$ into $\gamma$-$Fe_2O_3$. In contrast, the pigment containing magnesium which is prepared according to Example 8 showed no change up to a temperature of 260° C.

Use Example

A compact powder for use in make-up has the following composition and is made by conventionally mixing the following:

| | |
|---|---|
| Pigment of Example 5 | 30% by weight |

| | |
|---|---|
| Talc | 52.5% by weight |
| Kaolin | 3% by weight |
| Calcium stearate | 5% by weight |
| Corn starch | 3% by weight |
| Isopropyl laurate | 5% by weight |
| Isopropyl myristate | 1% by weight |
| Perfume | 0.5% by weight |

In the cosmetic thus prepared, the pigment of this invention has a better transparency and better filling and adhesion properties than the iron oxide pigments hitherto used.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A transparent, colored pigment comprising a platelet-shaped, transparent substrate, which is coated with a layer of colored metal oxides or metal hydroxides, and which layer contains 0.1–5% by weight of an alkaline earth metal oxide or hydroxide.

2. A pigment of claim 1 wherein the substrate is mica, talc or glass.

3. A pigment of claim 1 wherein the colored metal oxide or hydroxide is FeO(OH), Fe(OH)$_2$, Fe(OH)$_3$, Co(OH)$_2$, Cr(OH)$_3$, Fe$_2$O$_3$, Fe$_3$O$_4$, CoO or Cr$_2$O$_3$.

4. A pigment of claim 1 wherein the layer further contains Al$_2$O$_3$, ZnO or TiO$_2$.

5. A pigment of claim 1 wherein the alkaline earth metal is calcium, magnesium or barium.

6. A pigment of claim 1 wherein the substrate has a particle size of 1–100 μm.

7. A process for the preparation of a transparent, colored pigment comprising a platelet-shaped, transparent substrate, which is coated with a layer of a colored metal oxide or metal hydroxide, and which layer contains 0.1–5% by weight of an alkaline earth metal oxide or hydroxide;

comprising adding a base to a suspension of a platelet-shaped, transparent substrate in an aqueous solution of a soluble salt of the metal in said colored metal oxide or hydroxide and a soluble alkaline earth metal salt thereby coating the substrate with a colored metal oxide or hydroxide and an alkaline earth metal oxide or hydroxide; separating off the substrate and drying it.

8. A process of claim 7 further comprising calcining the coated substrate.

9. A process of claim 7 further comprising washing the separated substrate.

10. A process of claim 7 wherein the base is urea.

11. A process of claim 7 wherein the alkaline earth metal salt is MgSO$_4$, MgCl$_2$ or CaCl$_2$.

12. In a colored composition comprising a base ingredient and a coloring agent, the improvement wherein the coloring agent is a colored pigment of claim 1.

* * * * *